United States Patent [19]

Chang et al.

[11] 4,214,107

[45] Jul. 22, 1980

[54] HYDRATION OF OLEFINS USING ZEOLITE CATALYSTS

[75] Inventors: Clarence D. Chang, Princeton; Norman J. Morgan, Burlington, both of N.J.

[73] Assignee: Mobil Oil Corporation, New York, N.Y.

[21] Appl. No.: 919,194

[22] Filed: Jun. 26, 1978

[51] Int. Cl.² ............................................. C07C 29/04
[52] U.S. Cl. ................................................... 568/897
[58] Field of Search ......................................... 568/897

[56] References Cited

U.S. PATENT DOCUMENTS

| | | |
|---|---|---|
| 2,845,463 | 7/1958 | Friedman et al. .................... 568/897 |
| 3,173,855 | 3/1965 | Miale ..................................... 568/897 |
| 3,440,293 | 4/1969 | Rosscup et al. ....................... 568/897 |
| 3,702,886 | 11/1972 | Argaver et al. ...................... 423/328 |
| 3,709,979 | 1/1973 | Chu ................................... 252/455 Z |
| 3,832,449 | 8/1974 | Rosinski et al. ................. 252/455 Z |
| 4,016,245 | 4/1977 | Plank et al. ........................... 423/329 |
| 4,046,859 | 9/1977 | Plank et al. ...................... 252/455 Z |

*Primary Examiner*—Joseph E. Evans
*Attorney, Agent, or Firm*—Charles A. Huggett; Vincent J. Frilette

[57] ABSTRACT

A process for directly hydrating linear olefins having up to 4 carbon atoms to form alcohols, catalyzed by a novel class of highly siliceous zeolites exemplified by HZSM-5.

1 Claim, No Drawings

4,214,107

HYDRATION OF OLEFINS USING ZEOLITE CATALYSTS

BACKGROUND OF THE INVENTION

1. Field of the Invention

This invention relates to the production of alcohols by the direct hydration of the lower linear olefins, ethylene, propylene, and n-butenes. It relates particularly to the preparation of isopropyl alcohol from propylene. Still more particularly, it relates to a process for hydrating $C_2$–$C_4$ olefins in the presence of a crystalline aluminosilicate zeolite catalyst having a silica to alumina ratio of at least 12, and a Constraint Index hereinbelow defined of 1 to 12, such crystalline zeolite catalyst being exemplified by HZSM-5.

2. Prior Art

The production of isopropyl alcohol by reaction of the olefin with sulfuric acid is an old and widely practiced process. Nevertheless, it has several serious disadvantages, the more important of these being the corrosiveness of the acid, the necessity of diluting the acid to recover the alcohol product, and the consequent necessity to reconcentrate the acid prior to recycling to the process. Because of these disadvantages, it has been proposed to directly hydrate olefins in the presence of various solid catalysts. Phosphoric acid deposited on silica gel or clay, as well as tungsten oxide, are typical examples of such previously proposed solid catalysts. However, while these catalysts obviate the handling problems associated with sulfuric acid, they in turn tend to introduce new complications, notably the production of comparatively large amounts of undesirable polymer and ketone. Phosphoric acid in particular also is eluted during the process and requires that makeup acid be added to the feed to maintain catalyst activity. Furthermore, such prior catalysts have generally required temperatures in excess of about 500° F. to obtain reasonably satisfactory yields and selectivities. (See Brennstoff Chemie 34, 330, 1953.) The use of organic ion-exchange resins of the sulfonic acid type is described in U.S. Pat. No. 2,813,908 issued Nov. 19, 1957. Such resins are unstable above temperatures of 150° C. U.S. Pat. No. 3,076,039 issued Jan. 29, 1963 describes the use of molybdenum-promoted silica-alumina catalyst to convert propylene to isopropanol. U.S. Pat. No. 3,760,024 issued Sept. 18, 1973, discloses the conversion of $C_2$–$C_4$ paraffins and/or olefins to aromatic hydrocarbons with a crystalline aluminosilicate of the ZSM-5 type, at a temperature of 100° to 700° C.

BRIEF SUMMARY OF THE INVENTION

It has now been found that the lower straight chain olefins having up to 4 carbon atoms are selectively and efficiently directly hydrated to the corresponding alcohols by catalytic contact with a novel class of highly siliceous crystalline aluminosilicate zeolites exemplified by HZSM-5 under the specified reaction conditions described hereinbelow. This is surprising in view of the conversion of lower olefins to hydrocarbons in the absence of water and in the presence of the catalyst used in the present invention, as described in U.S. Pat. No. 3,760,024. The reaction of this invention is exemplified by the hydration of propylene which forms isopropanol without the concomittant formation of acetone and diisopropyl ether.

DETAILED DESCRIPTION OF THE INVENTION

The present invention is applicable to the hydration of normal monoolefins in the $C_2$–$C_4$ range. Accordingly, the invention is applicable to the hydration of ethylene, propylene, n-butene-1 and cis and trans n-butene-2. The term "normal butenes" is used herein to refer to any one of the foregoing four-carbon olefins and mixtures thereof, all of which produce secondary butanol on hydration. Substantially pure olefins, i.e., olefins of at least 90 weight % purity, may be charged to the process of this invention. Also useful for the purpose of this invention are hydrocarbon fractions which contain substantial amounts, e.g. about 25 to about 90 weight %, of ethylene, propylene, normal butenes, or suitable mixtures thereof. It is most desirable that the charge to the process of this invention be substantially free of substances such as benzene which react with normal olefins in the $C_2$–$C_4$ range since these diminish the alcohol yield.

When substantial amounts of isobutylene are present in the feed in admixture with normal olefins, it may be desirable to treat the mixture first to remove the isobutylene. It is well known in the art that isobutylene is a highly reactive olefin. Thus, it may be removed by contact under relatively mild conditions with an acidic solid which catalyzes the formation of isobutylene polymer. Alternatively, the isobutylene may be selectively hydrated under mild conditions to form tertiary butyl alcohol which is then easily separated from the linear olefins. Such a hydration procedure is described in U.S. Pat. No. 2,477,380.

In conducting the process of this invention, the hydrocarbon feed and water or steam are passed over the catalyst together at a hydrocarbon feed rate corresponding to a space velocity based on liquid olefin in the range of about 0.25 to 10 volumes of liquid olefin per volume of catalyst per hour, i.e. about 0.25 to 10 L.H.S.V., or at a gas hourly space velocity corresponding to equivalent contact time. The olefin to water mole ratio may be in the range of about 0.1 to 2.0, and is preferably in the range of 0.5 to 1.5. The total pressure in the reactor may range from about 50 p.s.i.g. to about 1500 p.s.i.g., with the temperature in the range of about 80° C. to about 400° C. The temperature chosen for the reaction depends on the reactivity of the olefin. Propylene and the butenes are considerably more reactive than ethylene, and for the former hydrocarbons a temperature in the range of about 100° to about 240° C. is necessary. Above 240° C. the propylene or butenes are converted in part to higher molecular weight hydrocarbons, while in the range of 100° to about 240° C. excellent reactivity and selectivity to isopropyl alcohol are observed. The hydration of ethylene, which is less reactive than propylene, requires a temperature in the range of about 240° to about 400° C.

Since low temperatures are associated with high values of the equilibrium constant for alcohol formation, it is desirable to hydrate at the lowest temperature compatible with a reasonable rate of conversion. As will be illustrated further by the examples, operation at the highly effective lower temperatures also serves to suppress or eliminate entirely the formation of hydrocarbon by-products. The reaction preferably is conducted in what is generally known in the art as a "trickle-bed" reactor, with at least a portion of the water in liquid phase.

Crystalline Aluminosilicate Zeolites

The crystalline aluminosilicate zeolites utilized herein are members of a novel class of zeolites that exhibits unusual properties. Although these zeolites have unusually low alumina contents, i.e., high silica to alumina ratios, they are very active even when the silica to alumina ratio exceeds 30. The activity is surprising since catalytic activity is generally attributed to framework aluminum atoms and/or cations associated with these aluminum atoms. These zeolites retain their crystallinity for long periods in spite of the presence of steam at high temperature which induces irreversible collapse of the framework of other zeolites, e.g. of the X and A type. Furthermore, carbonaceous deposits, when formed, may be removed by burning at higher than usual temperatures to restore activity. These zeolites, used as catalysts, generally have low coke-forming activity and therefore are conducive to long times on stream between regenerations by burning with oxygen-containing gas such as air.

An important characteristic of the crystal structure of this class of zeolites is that it provides constrained access to and egress from the intracrystalline free space by virtue of having an effective pore size intermediate between the small pore Linde A and the large pore Linde X, i.e. the pore windows of the structure have about a size such as would be provided by 10-membered rings of oxygen atoms. It is to be understood, of course, that these rings are those formed by the regular disposition of the tetrahedra making up the anionic framework of the crystalline aluminosilicate, the oxygen atoms themselves being bonded to the silicon or aluminum atoms at the centers of the tetrahedra. Briefly, the preferred type zeolites useful in this invention possess, in combination: a silica to alumina mole ratio of at least about 12; and a structure providing constrained access to the crystalline free space.

The silica to alumina ratio referred to may be determined by conventional analysis. This ratio is meant to represent, as closely as possible, the ratio in the rigid anionic framework of the zeolite crystal and to exclude aluminum in the binder or in cationic or other form within the channels. Although zeolites with a silica to alumina ratio of at least 12 are useful, it is preferred to use zeolites having higher ratios of at least about 30. Such zeolites, after activation, acquire an intracrystalline sorption capacity for normal hexane which is greater than that for water, i.e., they exhibit "hydrophobic" properties. It is believed that this hydrophobic character is advantageous in the present invention.

The zeolites useful in this invention have an effective pore size such as to freely sorb normal hexane. In addition, the structure must provide constrained access to larger molecules. It is sometimes possible to judge from a known crystal structure whether such constrained access exists. For example, if the only pore windows in a crystal are formed by 8-membered rings of oxygen atoms, then access by molecules of larger cross-section than normal hexane is excluded and the zeolite is not of the desired type. Windows of 10-membered rings are preferred, although in some instances excessive puckering of the rings or pore blockage may render these zeolites ineffective. Twelve-membered rings usually do not offer sufficient constraint to produce the advantageous conversions, although the puckered 12-ring structure of TMA offretite shows constrained access. Other 12-ring structures may exist which, due to pore blockage or to other cause, may be operative.

Rather than attempt to judge from crystal structure whether or not a zeolite possesses the necessary constrained access to molecules larger than normal paraffins, a simple determination of the "Constraint Index" as herein defined may be made by passing continuously a mixture of an equal weight of normal hexane and 3-methylpentane over a small sample, approximately one gram or less, of zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 1000° F. for at least 15 minutes. The zeolite is then flushed with helium and the temperature adjusted between 550° F. and 950° F. to give an overall conversion between 10% and 60%. The mixture of hydrocarbons is passed at 1 liquid hourly space velocity (i.e., 1 volume of liquid hydrocarbon per volume of zeolite per hour) over the zeolite with a helium dilution to give a helium to total hydrocarbon mole ratio of 4:1. After 20 minutes on stream, a sample of the effluent is taken and analyzed, most conveniently by gas chromotography, to determine the fraction remaining unchanged for each of the two hydrocarbons.

The "Constraint Index" is calculated as follows:

$$\text{Constraint Index} = \frac{\log_{10}(\text{fraction of n-hexane remaining})}{\log_{10}(\text{fraction of 3-methylpentane remaining})}$$

The Constraint Index approximates the ratio of the cracking rate constants for the two hydrocarbons. Zeolites suitable for the present invention are those having a Constraint Index of 1 to 12. Constraint Index (CI) values for some typical zeolites are:

| CAS | C.I. |
|---|---|
| ZSM-5 | 8.3 |
| ZSM-11 | 8.7 |
| ZSM-12 | 2 |
| ZSM-35 | 4.5 |
| ZSM-38 | 2 |
| TMA Offretite | 3.7 |
| Beta | 0.6 |
| ZSM-4 | 0.5 |
| H-Zeolon (mordenite) | 0.4 |
| REY | 0.4 |
| Amorphous Silica-Alumina | 0.6 |
| Erionite | 38 |

The above-described Constraint Index is an important and even critical definition of those zeolites which are useful in the instant invention. The very nature of this parameter and the recited technique by which it is determined, however, admit of the possibility that a given zeolite can be tested under somewhat different conditions and thereby have different Constraint Indexes. Constraint Index seems to vary somewhat with severity of operation (conversion) and the presence or absence of binders. Therefore, it will be appreciated that it may be possible to so select test conditions to establish more than one value in the range of 1 to 12 for the Constraint Index of a particular zeolite. Such a zeolite exhibits the constrained access as herein defined and is to be regarded as having a Constraint Index of 1 to 12. Also contemplated herein as having a Constraint Index of 1 to 12 and therefore within the scope of the novel class of highly siliceous zeolites are those zeolites which, when tested under two or more sets of conditions within the above specified ranges of temperature and conversion, produce a value of the Constraint Index slightly less than 1, e.g. 0.9, or somewhat greater than 12, e.g. 14 or 15, with at least one other value of 1 to 12. Thus, it should be understood that the Constraint Index value as used herein is an inclusive rather than an exclusive value. That is, a zeolite when tested by any combination of conditions within the testing definition set forth hereinabove to have a Constraint Index of 1 to 12 is intended to be included in the instant catalyst definition regardless that the same identical zeolite tested under other defined conditions may give a Constraint Index value outside of 1 to 12.

The class of zeolites defined herein is exemplified by ZSM-5, ZSM-11, ZSM-12, ZSM-35, ZSM-38, and other similar materials. U.S. Pat. No. 3,702,886 describing and claiming ZSM-5 is incorporated herein by reference.

ZSM-11 is more particularly described in U.S. Pat. No. 3,709,979, the entire content of which is incorporated herein by reference.

ZSM-12 is more particularly described in U.S. Pat. No. 3,832,449, the entire content of which is incorporated herein by reference.

ZSM-35 is more particularly described in U.S. Pat. No. 4,016,245, the entire content of which is incorporated herein by reference.

ZSM-38 is more particularly described in U.S. Pat. No. 4,046,859, the entire content of which is incorporated herein by reference.

The specific zeolites described, when prepared in the presence of organic cations, are substantially catalytically inactive, possibly because the intracrystalline free space is occupied by organic cations from the forming solution. They may be activated by heating in an inert atmosphere at 1000° F. for one hour, for example, followed by base exchange with ammonium salts followed by calcination at 1000° F. in air. The presence of organic cations in the forming solution may not be absolutely essential to the formation of this type zeolite; however, the presence of these cations does appear to favor the formation of this special class of zeolite. More generally, it is desirable to activate this type catalyst by base exchange with ammonium salts followed by calcination in air at about 1000° F. for from about 15 minutes to about 24 hours.

Natural zeolites may sometimes be converted to this type zeolite catalyst by various activation procedures and other treatments such as base exchange, steaming, alumina extraction and calcination, in combinations. Natural minerals which may be so treated include ferrierite, brewsterite, stilbite, dachiardite, epistilbite, heulandite, and clinoptilolite. The preferred crystalline aluminosilicates are ZSM-5, ZSM-11, ZSM-12, ZSM-35, and ZSM-38, with ZSM-5 being particularly preferred.

In a preferred aspect of this invention, the zeolites hereof are selected as those having a crystal framework density, in the dry hydrogen form, of not less than about 1.6 grams per cubic centimeter. It has been found that zeolites which satisfy all three of these criteria are most desired for several reasons. When hydrocarbon products or by-products are catalytically formed, for example, such zeolites tend to maximize the production of gasoline boiling range hydrocarbon products. Therefore, the preferred zeolites of this invention are those having a Constraint Index as defined above of about 1 to about 12, a silica to alumina ratio of at least about 12 and a dried crystal density of not less than about 1.6 grams per cubic centimeter. The dry density for known structures may be calculated from the number of silicon plus aluminum atoms per 1000 cubic Angstroms, as given, e.g., on Page 19 of the article on Zeolite Structure by W. M. Meier. This paper, the entire contents of which are incorporated herein by reference, is included in "Proceedings of the Conference on Molecular Sieves, London, April 1967," published by the Society of Chemical Industry, London, 1968. When the crystal structure is unknown, the crystal framework density may be determined by classical pyknometer techniques. For example, it may be determined by immersing the dry hydrogen form of the zeolite in an organic solvent which is not sorbed by the crystal. Or, the crystal density may be determined by mercury porosimetry, since mercury will fill the interstices between crystals but will not penetrate the intracrystalline free space. It is possible that the unusual sustained activity and stability of this class of zeolites is associated with its high crystal anionic framework density of not less than about 1.6 grams per cubic centimeter. This high density must necessarily be associated with a relatively small amount of free space within the crystal, which might be expected to result in more stable structures. This free space, however, is important as the locus of catalytic activity.

Crystal framework densities of some typical zeolites including some which are not within the purview of this invention are:

| Zeolite | Void Volume | Framework Density |
| --- | --- | --- |
| Ferrierite | 0.28 cc/cc | 1.76 g/cc |
| Mordenite | .28 | 1.7 |
| ZSM-5, -11 | .29 | 1.79 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

When synthesized in the alkali metal form, the zeolite is conveniently converted to the hydrogen form, generally by intermediate formation of the ammonium form as a result of ammonium ion exchange and calcination of the ammonium form to yield the hydrogen form. In addition to the hydrogen form, other forms of the zeolite wherein the original alkali metal has been reduced to less than about 1.5 percent by weight may be used. Thus, the original alkali metal of the zeolite may be replaced by ion exchange with other suitable ions of Groups IB to VIII of the Periodic Table, including, by way of example, nickel, copper, zinc, palladium, calcium or rare earth metals.

In practicing the desired conversion process, it may be desirable to incorporate the above described crystalline aluminosilicate zeolite in another material resistant to the temperature and other conditions employed in the process. Such matrix materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be composited with the zeolite include those of the montmorillonite and kaolin families, which families include the sub-bentonites and the kaolins commonly known as Dixie, McNamee-Georgia and Florida clays or others in which the main mineral constitutent is halloysite, kaolinite, dickite, nacrite or anauxite. Such clays can be used in the raw state as originally mined or initially subjected to calcination, acid treatment or chemical modification.

In addition to the foregoing materials, the zeolites employed herein may be composited with a porous matrix material, such as alumina, silica-alumina, silica-magnesia, silica-zirconia, silica-thoria, silica-berylia, silica-titania as well as ternary compositions, such as silica-alumina-thoria, silica-alumina-zirconia, silica-alumina-magnesia and silica-magnesia-zirconia. The matrix may be in the form of a cogel. The relative proportions of zeolite component and inorganic oxide gel matrix on an anhydrous basis may vary widely with the zeolite content ranging from between about 1 to about 99 percent by weight and more usually in the range of about 5 to about 80 percent by weight of the dry composite.

EXAMPLES

The examples which follow are illustrative of the present invention and are not to be construed as limiting in any manner the invention as defined in the present specification and claims. Unless specified otherwise in the examples themselves, all quantities and ratios are to be understood to refer to weights and ratios of weights.

EXAMPLES 1–5

A fixed-bed microreactor made from 0.25 inch O.D. (0.18 inch I.D.) 304 stainless steel tubing was loaded with 2 cc. of HZSM-5 zeolite pellets which had been calcined at 1000° F. for 16 hours. The reaction zone was electrically heated. Propylene and water were metered in separately. The reaction was run at different temperatures and pressures to show the effect of these variables. Reaction pressure was maintained with a backpressure regulator at the reactor exit. Products were analyzed by gas chromatography with the results shown in Table I. The age of the catalyst at the time the product sample was taken is indicated in the Table.

TABLE I

| EXAMPLE NO. | 1 | 2 | 3 | 4 | 5 |
|---|---|---|---|---|---|
| REACTION CONDITIONS | | | | | |
| T°,C. | 150 | 201 | 200 | 202 | 254 |
| P, psig | 130 | 130 | 130 | 255 | 120 |
| LHSV, hr$^{-1}$ | 1.5 | 1.5 | 1.5 | 1.5 | 1.5 |
| H$_2$O/HC, Mol Ratio | 0.9 | 0.9 | 0.9 | 0.9 | 0.9 |
| TIME ON STREAM (Days) | 1 | 2 | 7 | 8 | 3 |
| Conversion, % | 0.24 | 1.88 | 1.85 | 3.54 | 1.02 |
| Equil. Conv., % (calc'd.) | 17.34 | 4.67 | 4.67 | 8.16 | 1.24 |
| % Appr. to Equil. | 1.4 | 40.3 | 39.6 | 43.4 | — |
| PRODUCTS, Wt% | | | | | |
| Isopropyl Alcohol | 100 | 100 | 100 | 100 | 16.2 |
| Diisopropyl Ether | none | none | none | none | none |
| Hydrocarbon Byproduct | none | none | none | none | 83.8 |

EXAMPLE 6

This experiment was performed in a reactor similar to that used in Examples 1–5, with HZSM-5 catalyst pretreated as above described. Ethylene at the rate of 4000 gas hourly space velocity (i.e. volumes of gas S.T.P. per volume of catalyst per hour) was passed over the catalyst maintained at 325° C. Reaction pressure was 430 psig. Water was fed to provide a mol ratio of H$_2$O/HC of about 0.8. With catalyst that had been aged three days on stream, 0.8 wt.% of ethylene was found to be converted to ethanol. The calculated equilibrium conversion for the reaction conditions which obtained was 3.0%. No diethyl ether or hydrocarbon by-product was found on analysis of the product.

What is claimed is:

1. A process for directly hydrating propylene to isopropyl alcohol, which comprises contacting a mixture of propylene and water, said mixture having a mole ratio of propylene to water in the range of 0.5 to 1.5, with a synthetic crystalline aluminosilicate catalyst consisting essentially of HZSM-5, said contacting being conducted at a temperature of about 100° to about 240° C., a pressure from about 50 p.s.i.g. to 1500 p.s.i.g, and at a space velocity based on liquid olefin of about 0.25 to 10 LHSV, whereby directly forming isopropyl alcohol substantially free of ether and hydrocarbon by-product.

* * * * *